United States Patent [19]

Lumsden

[11] Patent Number: 4,753,113

[45] Date of Patent: Jun. 28, 1988

[54] MEASUREMENT OF THE STIFFNESS OF PACKET BLANK CREASES

[75] Inventor: William Lumsden, Winchester, England

[73] Assignee: British-American Tobacco Company Limited, London, England

[21] Appl. No.: 927,748

[22] Filed: Nov. 6, 1986

[30] Foreign Application Priority Data

Nov. 7, 1985 [GB] United Kingdom ............... 8527459

[51] Int. Cl.⁴ .............................................. G01N 3/20
[52] U.S. Cl. .................................................. 73/849
[58] Field of Search ............... 73/849, 850, 851, 852, 73/853, 854, 159; 493/37

[56] References Cited

U.S. PATENT DOCUMENTS

| | | | |
|---|---|---|---|
| 1,200,086 | 10/1916 | Cruser | 73/851 |
| 2,338,338 | 1/1944 | Kieckhefer | 73/854 |
| 2,482,470 | 9/1949 | Waard et al. | 73/849 |
| 4,046,001 | 9/1977 | Maeda et al. | 73/853 |
| 4,358,962 | 11/1982 | Ashby et al. | 73/849 |
| 4,578,052 | 3/1986 | Engel et al. | 73/159 |

Primary Examiner—Stewart J. Levy
Assistant Examiner—Robert R. Raevis
Attorney, Agent, or Firm—Kane, Dalsimer, Sullivan, Kurucz, Levy, Eisele and Richard

[57] ABSTRACT

Apparatus for measuring the stiffness of creases of a packet blank comprises first and second spaced apart guides, on which a flat blank may be supported, and a plunger which is movable between the guides to deform the blank about a crease(s). The plunger brings part of the blank into contact with a bearing surface, and a panel(s) bent relatively of that part rests against force measuring means. The force measuring means provides a signal indicative of the resistance to bending of a crease about which the panel(s) has been bent.

6 Claims, 2 Drawing Sheets

MEASUREMENT OF THE STIFFNESS OF PACKET BLANK CREASES

BACKGROUND OF THE INVENTION

1. Field of the Invention

The present invention relates to the stiffness measurement of creases in packet blanks.

2. Brief Description of the Prior Art

Pre-formed creases in packet blanks of carton board or similar material must be of acceptable stiffness or problems, expensive in terms of down time costs, are likely to occur in the operation of packaging machines to which the blanks are fed. Thus if a crease is of too great a stiffness value, an adhesive seam involving a panel bounding the crease may spring open. Such failure of the seam could lead to jamming of a packaging machine mechanism.

It is a common practice in the manufacture of blanks for hinged lid cigarette packets to form as many as fifty-six individual blanks from a single sheet of carton board. If it is desired to test for stiffness six creases of each blank, 336 crease tests must be made, and even this large number of tests yields for each of the fifty-six die stations only a single test value fo reach of the creases. Using presently available test apparatus capable of testing only one crease at a time and requiring prior preparations of a test specimen cut from the blank, the attainment of test data is very time consuming. Moreover, presently available crease stiffness test apparatus is not capable of providing adequate running efficiency predictors of modern high-speed packaging machinery.

SUMMARY OF THE INVENTION

The present invention provides crease stiffness measuring apparatus comprising first and second spaced apart guide means, bearing means and force measuring means to one side of said first and second guide means, plunger means movable in a line of movement extending between said first and second guide means towards and away from said bearing means whereby when said plunger means is moved towards said bearing means a packet blank placed in contact with said first and second guide means, in the side thereof remote said bearing means and said force measuring means, may be deformed about a crease line of said blank and a first portion of said blank extending from said crease line at one side of said crease line may be thereby brought into contact with said bearing means, and a second portion of said blank extending from said crease line at the other side of said crease line may be brought into force measuring contact with said force measuring means.

The apparatus may be constructed and arranged to provide stiffness measurement values for two crease lines of a packet blank, the apparatus being provided with first and second force measuring means. In such case the plunger means may be adapted to bring an intermediate portion of the blank extending from one to the other of the crease lines into contact with the bearing means. In the final deformed configuration of the blank, further portions of the blank extending from the crease lines at sides thereof remote the intermediate portion may be disposed substantially perpendicularly of the intermediate portion.

The apparatus may be constructed and arranged to provide stiffness measurement values for two or more portions of a packet blank each of which portions extends at the same side of a crease line of the blank as the other portion(s) and each of which portions is capable of deformation about the crease line independently of the other portion(s). In such case the apparatus comprises a separate force measuring means for force measuring contact with each of the portions.

Advantageously, each guide means is provided by a straight edge of a strip of rigid material. Suitably the first and second guide means extend parallel to each other.

For the majority of packet blanks it is advantageous for the bearing means, which suitably takes the form of a flat surface, to extend perpendicularly of the line of movement of the plunger means.

There may be provided a further guide means and associated force measuring means arranged for the stiffness measurement of a crease line extending transversely of the first crease line or lines.

In order that packet blanks of different dimensions may be accommodated provision may be made whereby the distance between the first and second guide means and between first and second force measuring means is adjustable.

It is desirable that there should be provided location means by which a packet blank can be accurately placed in a predetermined location relatively of the guide means.

Suitably, the or each force measuring means is a transducer operable to produce a force-representing electrical signal.

BRIEF DESCRIPTION OF THE DRAWINGS

In order that the present invention may be clearly understood and readily carried into effect reference will now be made to the drawings hereof, in which.

DETAILED DESCRIPTION OF THE INVENTION

Figure 1:
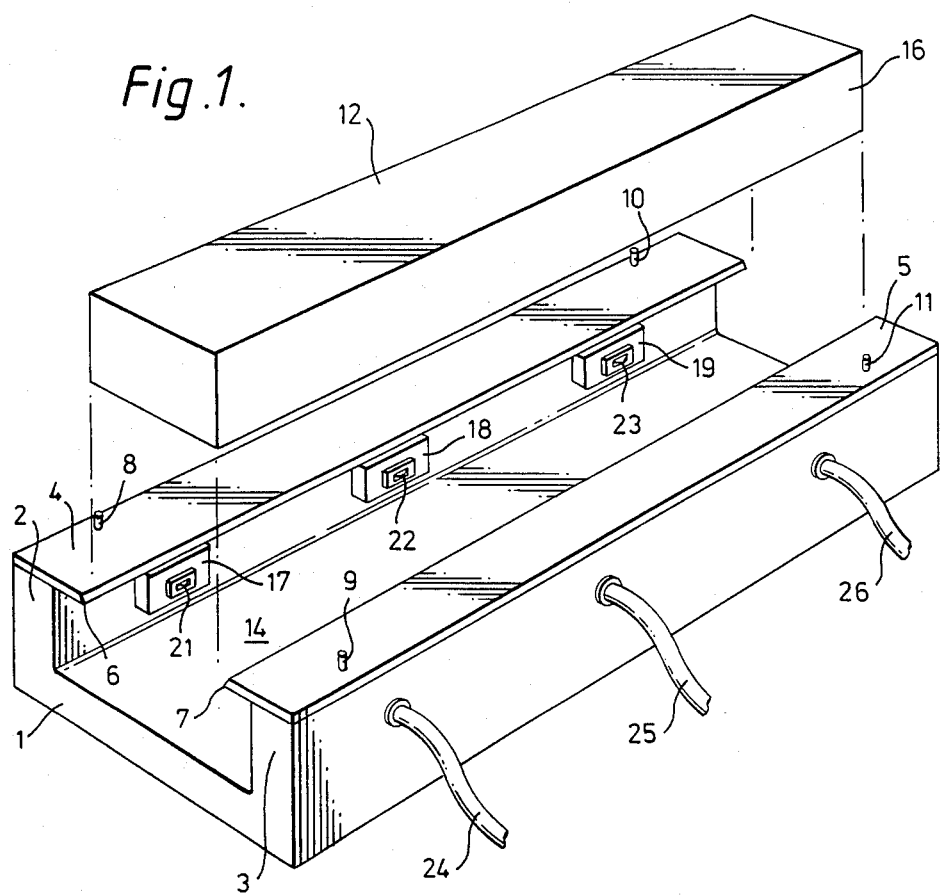
FIG. 1 shows a diagrammatic perspective view of a crease stiffness test apparatus.
Figure 2:
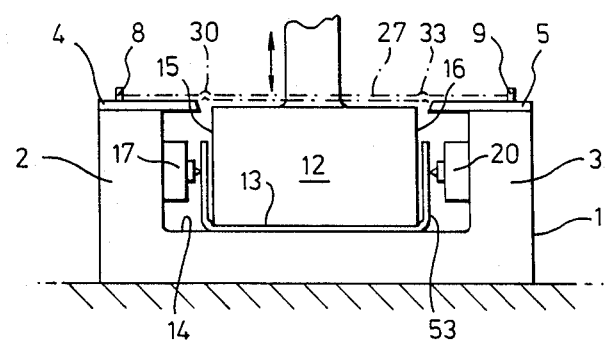
FIG. 2 shows an end view of the apparatus of FIG. 1.
Figure 3:
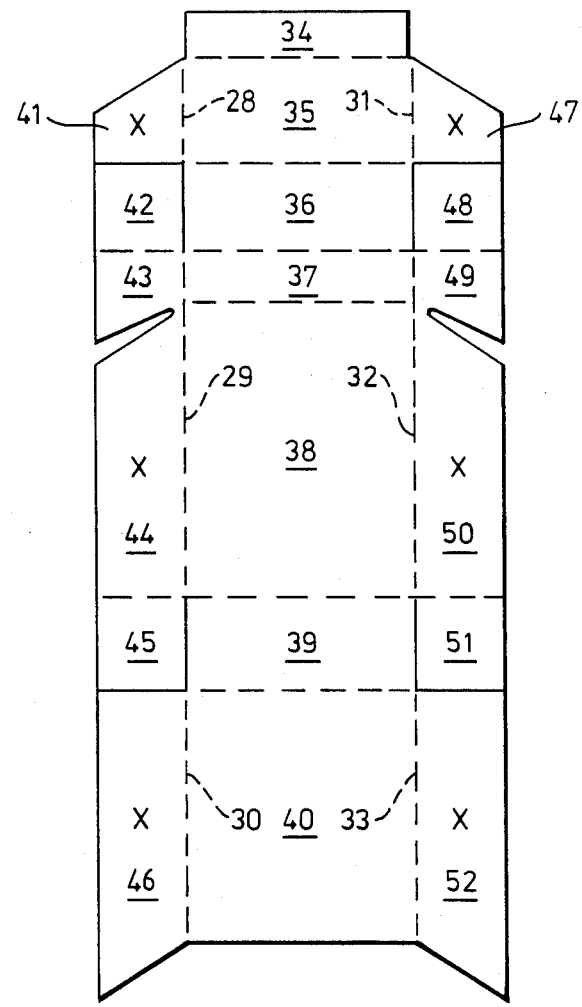
FIG. 3 shows a cigarette packet blank, with broken lines indicating creases and full lines within the perimeter of the blank indicating lines of cut.

The crease stiffness test apparatus of FIGS. 1 and 2 is adapted to measure the stiffness of creases of the hinged lid cigarette packet blank of FIG. 3. The apparatus comprises a rigid, metal bed 1 of U-section. Fixedly secured at upper surfaces of upwardly extending side members 2 and 3 of the bed 1 are guide plates 4 and 5. Inner bevelled edges 6 and 7 of the plates 4, 5 extend parallel to each other and provide first and second guide means. Pegs 8–11 upwardly extending from the plates 4, 5 provide location means for the blank of FIG. 3, ensuring that when the blank is placed in an initial flat condition of the plates 4, 5, the blank lies parallel with the edges 6, 7 of the plates 4, 5 and in a predetermined location relatively thereof.

The crease stiffness test apparatus also comprises a plunger block 12 which is movable, by moving means which for the sake of simplicity is not shown, vertically towards and away from bed 1. The block 12 is of rectangular cross-section and of a length the same as that of the bed 1. Under-surface 13 of the block 12 is at all times parallel to the plates 4, 5 and to base surface 14 of the bed 1. Vertical side faces 15 and 16 of the block 12 are at all times parallel to the edges 6, 7 of the plates 4, 5.

Spaced apart lengthwise of the bed 1 and secured at the inner face of each of the side member 2,3 thereof are three force transducers, those seen in FIG. 1 being designated by reference numerals 17, 18 and 19 respectively and those seen in FIG. 2 being designated by reference numerals 17 and 20 respectively. Each of the force transducers comprises a movable point contact member, those of the transducers 17–19 being respectively designated by reference numbers 21–23. The contact members are located at a common distance from surface 14. Leads extend, via bores in the side members 2, 3, from the force transducers to programmable processing means (not shown), the leads associated respectively with transducer 20 and th eother two transducers secured to side member 3 being shown in FIG. 1 and being designated by reference numerals 24–26.

In use of the crease stiffness test apparatus the plunger block 12 is raised to a level above the guide plates 4, 5 and the flat blank of FIG. 3 is placed on the plates 4, 5. Correct positioning of the blank is assured by abutment of side edges of the blank against the pins 8–11. The blank in this initial position is indicated in broken line in FIG. 2 and is designated by reference numeral 27. The spacing of the plates 4, 5 is such that lengthwise extending creases 28–30 and 31–33 of the blank although not overlying the plates 4, 5 are disposed immediately adjacent the inner edges 6, 7 of the plates 4, 5.

When the plunger block 12 is lowered, the undersurface 13 of the block 12 contacts panels 34–40 of the blank, which panels are disposed between the lines along which extend the creases 28–30 and 31–33. The width of the block 12 is such that the block 12 extends to, but does not overlie, the creases 28–30 and 31–33.

As the block 12 passes downwardly between the plates 4, 5, side panels 41–46 and 47–52 are moved upwardly by contact with the bevelled inner edges 6, 7 of the plates 4, 5. In the final position and configuration of the blank, as shown in full line in FIG. 2 with reference numeral designation 53, panels 34–40 are sandwiched between the under-surface 13 of the block 12 and the base surface 14 of the bed 1 and the side panels extend upwardly and are substantially perpendicular to the panels 34–40. Side panels 41, 44 and 46 rest against contact members 21, 22 and 23 respectively. Thus electrical signals are produced by the force transducers 17–19, which signals are representative of the forces at the location of the contact member 21–23 resulting from the resiliency, i.e. resistance to bending, of the creases 28–30. Similarly, electrical signals passing along leads 24–26 are produced in the three transducers positioned opposite the transducers 17–19 and are representative of the resiliences of the creases 31–33.

The crosses in FIG. 3 indicate the points at which the transducer contact members contact side panels of the blank.

The U-form final configuration 53 of the blank is an appropriate one in that it is the same configuration as that to which the blank is brought in a cigarette packing machine. That the mode of operaiton of the test apparatus is appropriate is borne out by the fact that in use of the apparatus a crease resilience force for any one of the six tested creases which is in excess of a threshold value has been found to provide a high probability indicator of a packing machine running problem for all blanks produced at the die station which produced the test blank.

The programmable processing means to which the force indicative signals from the six force transducers are fed is preferably operable to store the values which the signals have assumed at the end of a predetermined time period from the arrival of the block 12 at its lowermost position. Fifteen seconds is, for example, an appropriate time period. The processing means is preferably programmed to produce for a batch of blanks a statistical value relating to each of the six creases, a means value or a standard deviation for example.

In order to accommodate blanks in which the distance apart of the lengthwise extending crease lines is different from the distance between the crease lines 28–30 and 31'33 of the blank of FIG. 3, the apparatus of FIGS. 1 and 2 may be modified by the provision of means whereby the plate 5, together with the force transducers secured to side member 3 may be moved in a direction towards and away from the plate 4 and the force transducers (17–19) secured to the side member 2.

If it should be required to measure the stiffness of the crease bounding the inner edge of tuck-in flap 34 of the blank of FIG. 3, the apparatus of FIGS. 1 and 2 may be provided, at the end thereof to the right as viewing FIG. 1, with a third guide means, having an inner edge perpendicular to and co-planar with the edges 6,7 of the plates 4,5, and with a further force transducer located for force measuring contact with the flap 34.

Whereas the transducer contact members are represented above as movable point contact members, advantageously they can also be elongate lines of contact extending parallel to the guide means, knife-edge contact members, for example.

I claim:

1. Crease resiliency force measuring apparatus comprising first and second spaced apart guide means, base support means and force measuring means, plunger means movable in a line of movement extending between said first and second guide means towards and away from said base support means whereby when said plunger means is moved towards said base support means a packet blank placed in contact with said first and second guide means, to the side thereof remote said base support means and said force measuring means, may be deformed about a crease line of said blank and a first portion of said blank extending from said crease line at one side of said crease line may be thereby brought into contact with said base support means, and a second portion of said blank extending from said crease line at the other side of said crease line may be brought into force measuring contact with said force measuring means.

2. Apparatus as claimed in claim 1, in which said first guide means extends parallel to said second guide means.

3. Apparatus as claimed in claim 1, in which said base support means extends perpendicularly of said line of movement of said plunger means.

4. Apparatus as claimed in claim 1, comprising further force measuring means disposed for force measuring contact with a third portion of said blank extending from a further crease line bounding a side of said first portion opposite the first mentioned crease line.

5. Apparatus as claimed in claim 1, comprising location means by which said blank can be placed in a predetermined location relatively of said first and second guide means.

6. A method of measuring crease resiliency, comprising; placing a packet blank, said blank having a crease line, a first portion and a second portion extending respectively to either side of the crease line, in contact with first and second guide means to one side of the blank; moving plunger means in a line of movement extending between said first and second guide means towards base support means located to that side of said guide means remote said plunger means so that said blank is deformed about said crease line; whereby said first portion of said blank is brought to and held at said base support means and said second portion of said blank is brought into contact with force measuring means operable to measure the resilient force exerted by said second portion.

* * * * *